United States Patent [19]
Nadeau et al.

[11] Patent Number: 5,882,870
[45] Date of Patent: Mar. 16, 1999

[54] RAPIDLY REVERSED THROMBIN BINDING OLIGONUCLEOTIDE ANTICOAGULANTS

[75] Inventors: James G. Nadeau, Chapel Hill; Erwin A. Vogler, Newhill, both of N.C.

[73] Assignee: Becton Dickinson and Company, Franklin Lakes, N.J.

[21] Appl. No.: 7,227

[22] Filed: Jan. 14, 1998

[51] Int. Cl.⁶ ............... C12Q 1/68; C12Q 1/56; C07H 21/04
[52] U.S. Cl. ............... 435/6; 435/13; 435/91.1; 536/23.1
[58] Field of Search ............... 435/6, 13, 91.1, 435/172.3, 320.1, 325; 536/23.1, 24.3

[56] References Cited

U.S. PATENT DOCUMENTS 5,476,766  12/1995  Gold et al. ................. 435/6
5,668,265  9/1997  Nadeau ..................... 536/23.1

OTHER PUBLICATIONS

DeAnda et al. Ann. Thorac. Surg. 58, 344–50 (1994).
Kubik, Mark F. et al., *Nucleic Acids Research;* 22, 13, pp. 2619–2626 (1994).
Bock, Louis C. et al., *Nature;* 355 pp. 564–566 (1992).

*Primary Examiner*—John L. LeGuyader
*Assistant Examiner*—Mark L. Shibuya
*Attorney, Agent, or Firm*—David W. Highet, Esq.

[57] ABSTRACT

The present invention relates to a system for the reversible anticoagulation of blood utilizing a nucleic acid ligand which binds thrombin and a reversing agent which has greater affinity for the nucleic acid ligand than does thrombin. When used with a blood sample, the nucleic acid ligand binds thrombin, preventing it from converting fibrinogen to fibrin, and thus anticoagulating the blood. Subsequently, the reversing agent may be added to the anticoagulated blood sample, and by competitive binding, replaces thrombin bound to the ligand, thus freeing the thrombin to convert fibrinogen to fibrin and allowing the blood to coagulate.

8 Claims, 2 Drawing Sheets

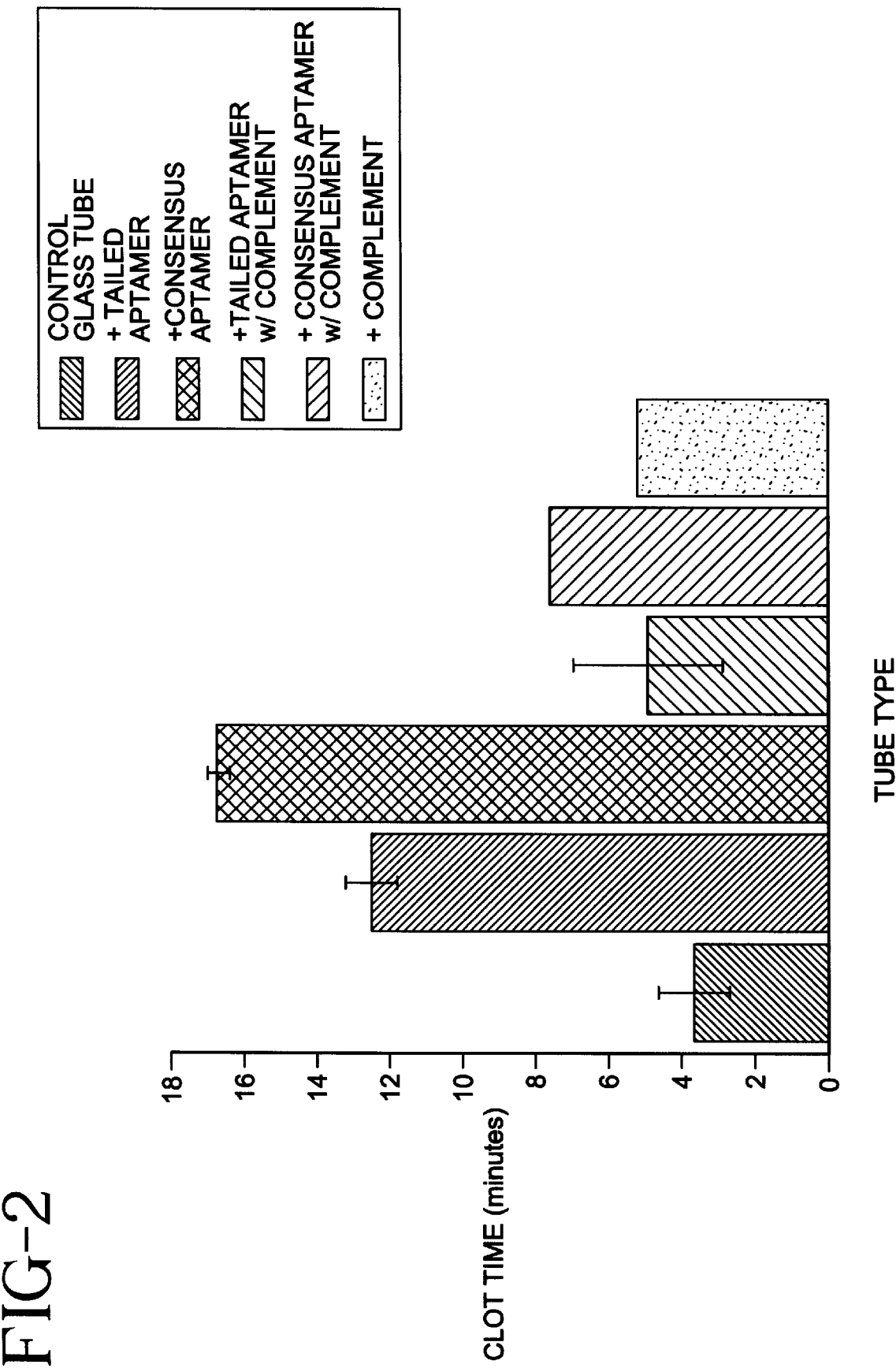

RAPIDLY REVERSED THROMBIN BINDING OLIGONUCLEOTIDE ANTICOAGULANTS

FIELD OF THE INVENTION

This invention relates to blood collection and, more particularly, relates to vacuum draw tubes or gravity flow tubes for blood sample collection and the use therein of additives for prevention of blood coagulation in the preparation of blood plasma or whole blood for both chemical and hematological testing. The invention also relates to diagnostic assays that utilize the protease enzyme thrombin as a means of amplifying signal.

BACKGROUND OF THE INVENTION

Blood samples are routinely taken in evacuated tubes, such as glass VACUTAINER® Brand evacuated sample collection tubes (Becton Dickinson and Company). One end of a double-ended needle is inserted into a patient's vein. The other end of the needle then punctures a septum covering the open end of the evacuated sample collection tube so that the vacuum in the tube draws the blood sample through the needle into the tube. Using this technique a plurality of samples can be taken using a single needle puncture of the skin. Plastic tubes have also been proposed for blood collection. Plastic offers several advantages related to lower breakage than glass tubes, less weight in shipment, and easier disposal by incineration for examples. Similarly, sample collection tubes designed for gravity based collection of smaller samples, such as a blood sample from an infant are also used with the same techniques. One such type of smaller tube is the MICROTAINER® Brand sample collection tube sold by Becton Dickinson and Company.

Blood samples collected in evacuated tubes are prepared for clinical examination in either the coagulated or non-coagulated (anticoagulated) state. In the latter category, which is the object of this invention, anticoagulation agents are utilized. There are a variety of anticoagulants routinely used in the art. These can be broadly classified as either calcium chelator or thrombin inhibitors. Calcium chelators function by removing calcium from solution in blood as a free ion. This inhibits coagulation because calcium is a necessary divalent ion for blood enzyme function. Citric acid, ethylenediaminetetraacetate (EDTA), fluorides, and oxalates are chemical anticoagulants that fall into calcium chelator category.

Thrombin is a serine protease derived from blood that converts fibrinogen to fibrin. Fibrin, in turn, polymerizes into a network that causes blood to gel or coagulate. As such, thrombin is a pivotal enzyme in hemostasis, and interruption of thrombin function can thus prevent blood coagulation. Thrombin inhibitors directly interfere with thrombin enzymatic function by blocking interaction with fibrinogen. Hirudin and heparin (through the antithrombin-heparin complex ATIII) are biochemical anticoagulants falling into the thrombin inhibitor category. Hirudin and heparin are well known in the field of hematology.

Calcium chelator and thrombin inhibitor anticoagulants have characteristic interferences with downstream clinical analysis. As examples, EDTA is successfully used in about 35% of hematology tubes (tripotassium, disodium, dipotassium, and liquid forms), but can induce blood cell aggregation. EDTA is not generally acceptable for use in nucleic acid diagnostics applying DNA amplification reactions such as polymerase chain reaction (PCR), which is important in growing markets of cellular analysis and viral load testing. Also, EDTA is inhibitory in T-cell stimulation assays. Oxalates can cause blood cells to shrink or expand, thus complicating cell volume measurements. Fluorides used in glucose testing are relatively poor anticoagulants and can cause hemolysis. Heparin can not be used in coagulation tubes because heparin interferes with enzymes of the coagulation cascade as well as with PCR.

Citrate is in widespread use for coagulation assays and is the anticoagulant of choice for PCR, but citrate causes some problems in cell or virus culture. Hirudin, a strong anticoagulant derived from leeches, and synthetic hirudin analogs are not yet in widespread commercial applications due to cost and availability.

Also, a nucleic acid ligands or aptamers to thrombin have been developed which inhibit coagulation of blood (Kubik, M. F. et al., Nuc. Acids Res. 22, 2619 (1994) and Bock L. C. et al., Nature 355, 564 (1992)). These nucleic acid ligands have not been used in any commercial products.

Another issue in anticoagulation is that of reversibility. In certain blood diagnostic tests it is useful to potentiate the coagulation cascade by reversing the anticoagulated state. For example, in the testing for blood coagulation dysfunctionality, it is customary in the art to use citrated blood plasma because the anticoagulated state can be rapidly reversed by addition of exogenous calcium which replenishes the necessary calcium for blood enzyme function. Anticoagulation of heparinized blood can be reversed by addition of heparinase, an enzyme that digests heparin and eliminates the coagulation-inhibiting heparin-ATIII complex. Unlike calcium and heparin, however, no reversing agents for hirudin are known. Thus hirudin is only appropriate for permanently anticoagulated blood specimens. Reversibility of the effects of nucleic acid ligands has also not been demonstrated in the art.

Blood testing would be significantly simplified if a single specimen of blood could be used for whole blood, plasma, and serum applications. Thus, there is need in the art for a "universal anticoagulant" that does not interfere with downstream clinical or hematological testing and is reversible by addition of a suitable reversing agent.

SUMMARY OF THE INVENTION

In order to address this need in the art, the present invention relates to a system for the reversible anticoagulation of blood utilizing a nucleic acid ligand which binds thrombin and a reversing agent which has greater affinity for the nucleic acid ligand than does thrombin. When used with a blood sample prior to addition of the reversing agent, the nucleic acid ligand of the system binds thrombin, and thus inhibits conversion of fibrinogen to fibrin, and consequently prevents blood coagulation or significantly decreases the rate of blood coagulation (i.e., increases clotting time). Subsequently, when coagulation of the blood is desired, the reversing agent is added to the system, and due to its greater affinity for the nucleic acid ligand causes the release of thrombin from the ligand through a competitive binding reaction. The released thrombin in the blood sample converts fibrinogen to fibrin allowing blood coagulation to occur.

A preferred reversing agent is an oligonucleotide with a sequence complementary to and of opposite polarity to that of the nucleic acid ligand. The reversing agent may also be optionally combined with a coagulation activator to enhance the rate of blood coagulation after reversing the anticoagulative effect of the thrombin ligand.

A second aspect of the invention is utilization of the system in a diagnostic test. This test is performed in such a way that a complex of thrombin bound to nucleic acid ligand and soluble fibrinogen are mixed with a sample which may, or may not contain an analyte of interest. Active thrombin is released from the complex in the presence of analyte. The released thrombin converts fibrinogen to fibrin, and gelation of fibrin and gelation time are used as indicators of the presence and concentration of analyte in the sample, respectively.

A third aspect of this invention is a blood collection assembly which utilizes the system. The assembly contains either an evacuated or non-evacuated blood collection tube having the reversible thrombin-binding nucleic acid ligand therein. A preferred assembly is a plastic tube having a closed end and an open end covered by a septum or other closure, which plastic tube may be either evacuated or non-evacuated.

BRIEF DESCRIPTION OF THE FIGURES

The various objects, advantages and novel features of the invention will be more readily appreciated from the following detailed description when read in conjunction with the appended figures, in which:

FIG. 2 is a graphic depiction of the reversibility of the anticoagulation effects of nucleic acid ligands which bind thrombin.

DETAILED DESCRIPTION OF THE PREFERRED EMBODIMENT OF THE INVENTION

Figure 1:
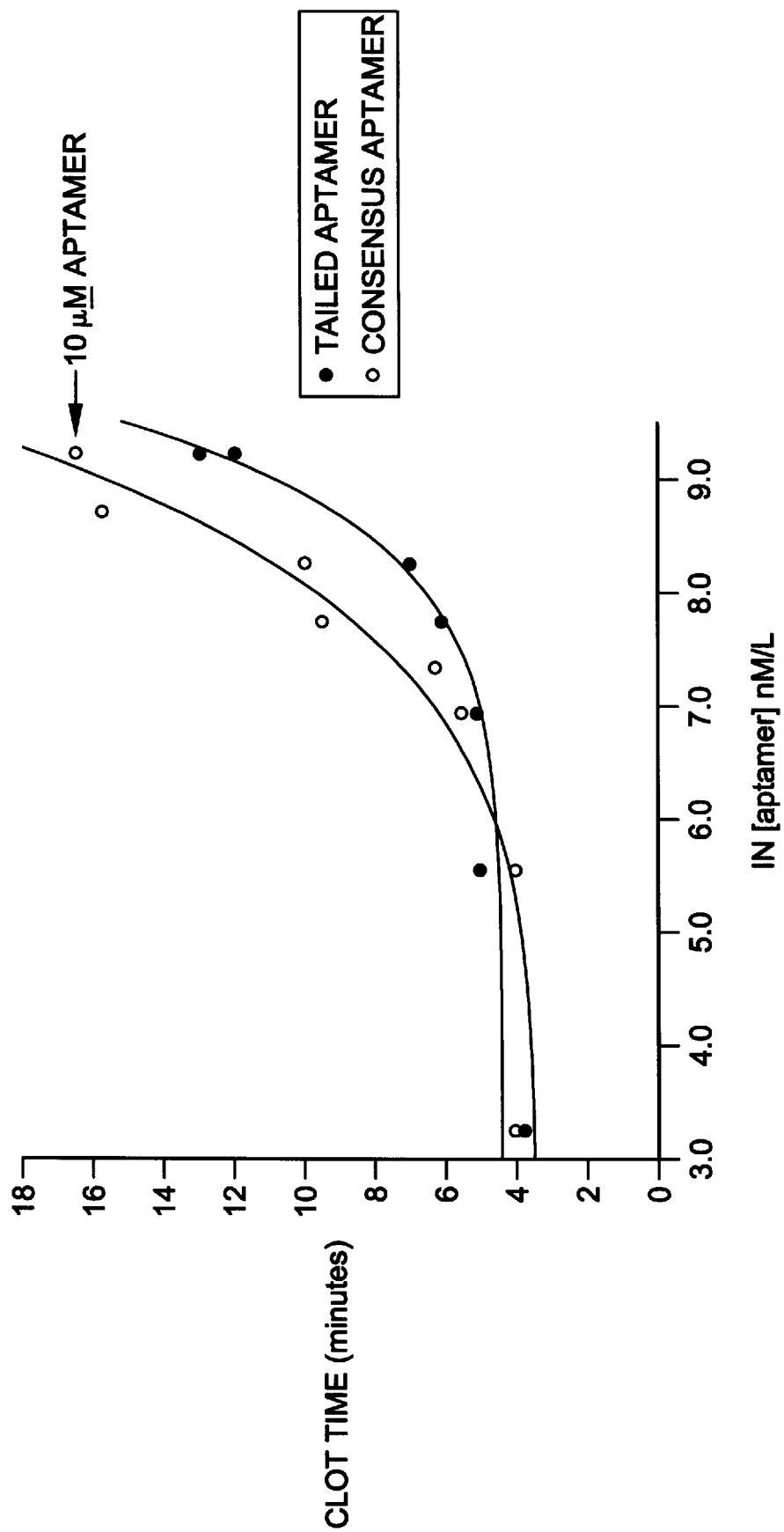
FIG. 1 is a graphic depiction of the inhibition of coagulation of plasma with varying amounts of two nucleic acid ligands.

While this invention is satisfied by embodiments in many different forms, there will herein be described in detail preferred embodiments of the invention, with the understanding that the present disclosure is considered as exemplary of the principles of the invention and is not intended to limit the invention the embodiments illustrated and described. The scope of the invention will be measured by the appended claims and their equivalents.

A new class of thrombin-binding anticoagulants based on oligonucleotide chemistry have been recently introduced (Bock, L. C. et al., *Nature* 355 564 (1992)). These protein-binding DNA or RNA molecules were discovered by screening combinatorial libraries of oligonucleotides for thrombin binding activity. Not unlike the conventional hirudin and heparin anticoagulants, these oligonucleotides are thought to inhibit thrombin activity by binding to the enzyme, thus blocking conversion of fibrinogen to fibrin.

Similarly, bi-directional nucleic acid ligands which bind thrombin have also been developed as more fully described in U.S. Pat. No. 5,668,265, the disclosure of which is specifically incorporated herein by reference. Bi-directional nucleic acid ligands are also referred to as oligonucleotides with inverted polarity, and are described as such in U.S. Pat. No. 5,399,676 also incorporated herein by reference. However, this patent does not describe any thrombin binding activity of the oligonucleotides with inverted polarity.

Briefly, bi-directional nucleic acid ligands are at least two oligonucleotides which are linked to one another through a binder or coupling moiety at their respective same terminii (i.e., 5' or 3' ends). Thus, bi-directional nucleic acid ligands have at least two 5' ends or 3' ends. Due to the presence of 3' exonucleases in blood, bi-directional nucleic acid ligands with 3' terminii connected to the linker compound, and thus, 5' exposed ends are particularly useful to bind thrombin because of their resistance to 3' exonuclease activity.

Protein-binding oligonucleotides may be in the form of extended chains (strands) of DNA or RNA molecules or in the form of more complex, folded structures stabilized by intermolecular forces between the purine or pyrimidine bases comprising these biopolymers (A-adenine, T=thymine, G=guanine, C=cytosine in DNA; A, G, C, and U=uracil in RNA). Typically, oligonucleotide ligands are relatively short chain lengths consisting of 25 or fewer base units. Bi-directional oligonucleotide ligands are also of about the same length. In the presence of a complimentary oligonucleotide sequence, the single-stranded structure of the uni-directional ligand is energetically unfavorable relative to an extended double-helix structure formed by complementary base pairing. Similarly, the single-stranded structure of the bi-directional nucleic acid ligand is energetically unfavorable relative to an extended double helix structure formed in the presence of a complimentary oligonucleotide sequence, which in this case will in general also need to be bi-directional in order to maintain the standard (i.e., anti-parallel) Watson-Crick complementarity across regions of inverted sequence polarity. For example, the oligonucleotide with Watson-Crick complementary to the bi-directional nucleic acid ligand compound  GGTTGGTTG³'X³'TTGGTTGG⁵' will be ³'CCAACCAAC⁵' 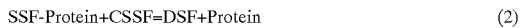 Y⁵'AACCAACC³', where X and Y are linking compounds (such as a phosphodiester group, glycerol, hexaethylene glycol, etc.) and X may or may not be identical to Y. If the nucleic acid ligand contains a 3'-3' linkage, then the complementary sequence will contain a 5'-5' linkage, and vice versa. However, typically, it is found that double-stranded, extended-chain oligonucleotide molecules are unable to bind protein.

The present invention is a system which utilizes the spontaneous formation of double-stranded DNA to inactivate protein binding of a single-stranded DNA ligand as illustrated in the following chemical reactions:

SSF+Protein=SSF-Protein (1)

SSF-Protein+CSSF=DSF+Protein (2)

where SSF represents the single-stranded nucleic acid ligand, CSSF is the complementary sequence to SSF, and DSF is the double-stranded form produced by pairing SSF with CSSF. In equation (1), the SSF ligand binds to protein, producing an inactivated protein-ligand complex (SSF-Protein). In equation (2), active protein is released from the inactive protein complex by pairing of SSF with CSSF in the formation of DSF. DSF is not a protein ligand and protein released from the SSF-Protein complex is in its active, native state.

A system as defined for purposes of the present invention includes reagents or components which have different, but related activities when contacted with, applied to, or used with a common sample. Such a system is used in a variety of applications for different purposes.

The system of the present invention is exemplary in that it includes two reagents, a thrombin binding nucleic acid ligand and a reversing agent. As related to the equations above, the ligand is SSF and the reversing agent is CSSF. These two reagents of the system have different, but related activities when contacted with a common sample, blood. Specifically, the ligand (SSF) causes anticoagulation of blood, and the reversing agent (CSSF) has the related activity of reversing blood anticoagulation. As explained in greater detail below, the specific system of the present invention is used in a variety of applications including evacuated and non-evacuated specimen or blood collection containers and diagnostic kits.

In application of the system as represented by strategy of equations (1) and (2) above to reversible anticoagulation of blood, the protein of reactions (1) and (2) is the enzyme thrombin, SSF is a oligonucleotide ligand to thrombin, and CSSF is the complementary sequence to that oligonucleotide ligand. A blood sample is collected in a tube or other container or vessel containing an amount of SSF that will bind all thrombin potentially present in the blood sample. It is well known in blood biochemistry that thrombin is generated from prothrombin on an equivalent molar basis. Since prothrombin concentration in normal blood is about 1.4 $\mu$M (Putnam, F. W., in *The Plasma Proteins,* 2d Edition, F. W. Putnam, Ed., Academic Press, New York, 1975, pp. 58–94), the maximum thrombin concentration that can be generated is also about 1.4 $\mu$M. Preferably, the SSF-to-prothrombin molar ratio would be between 0.1 and 100 and most preferably between 1 and 10.

The actual amount of SSF required depends on the binding capacity of the thrombin ligand and the amount of prothrombin released during collection and storage of the blood sample. Whereas the former is specific to the chemical nature of the thrombin ligand, the latter is dependent on the viability of blood and chemical nature of the container in which the blood is stored.

Preferably, the blood sample is stored in a hydrophobic plastic tube that does not stimulate rapid coagulation of blood. Exemplary hydrophobic plastic tubes are known to those skilled in the art, and are described in U.S. Pat. No. 5,318,806 to Montgomery et al., the disclosure of which is incorporated herein by reference. In contrast, commensurately more SSF would be required if the blood sample is stored in plain glass tubes which are known to stimulate blood coagulation.

Upon mixing the SSF with the blood sample, any thrombin available or produced from prothrombin is inactivated by its binding to SSF which is in excess relative concentration to thrombin. The resultant anticoagulated blood can then be used for hematological or chemical tests of whole blood or blood plasma.

Because subsequent tests of serum produced from coagulated blood may also be desired, anticoagulation which has resulted from the complex of SSF and thrombin can be reversed by addition of CSSF. The CSSF-to-SSF mole ratio is preferably between 0.01 and 10, and most preferably between 0.1 and 1. The reversing agent may optionally be a mixture of CSSF and a coagulation activating agent to enhance the rate of coagulation after reversing the anticoagulated state. Coagulation activators include, but are not limited to, crushed glass or plastic parts with an activating surface chemistry. Exemplary coagulation activators are known to those skilled in the art, and are described in U.S. Pat. No. 5,344,611 to Vogler et al. and U.S. Pat. No. 5,318,806 to Montgomery et al., both of which are incorporated herein by reference. Other coagulation activators include biochemical coagulation activators such as ellagic acid or thrombin itself. The reversing agent may be optionally carried on or immobilized onto a carrier bead or particle or sprayed into the blood collection tube or container.

The reversing agent need not be limited to complementary oligonucleotide sequences to SSF. The reversing agent may be selected from any material having greater binding affinity for SSF than thrombin such as inorganic complexes or proteins known to bind oligonucleotides. Examples of such materials include single-stranded DNA binding proteins as described by Chase, J. W. & Williams, K. R., *Ann. Rev. Biochem.* 56, 103 (1986); copper (II), mercury (II), silver(I) as described by Eichhorn, G. L. & Shin, Y. A., *J. Amer. Chem. Soc.* 90 7323–7328 (1968) and Dale, R. M. K. et al., *Biochemistry* 14, 2447–2457 (1975); and platinum complexes as described by Lippard, S. J., *Acc. Chem. Res.* 11, 211–217 (1978).

When utilizing the system of the present invention as a diagnostic test in accordance with equations (1) and (2) above, the protein is the enzyme thrombin, SSF is a oligonucleotide ligand to thrombin, and CSSF is the complementary sequence to that oligonucleotide ligand which is also the analyte of the diagnostic test. In such a diagnostic application, SSF-Protein and excess SSF are added to a fibrinogen mixture containing the sample to be analyzed. In the case where CSSF is present at a concentration sufficient to release protein (thrombin) from SSF-protein, free thrombin produces fibrin polymer from fibrinogen at a rate dependent on the release concentration. It will be readily apparent to those skilled in the art that fibrin polymer can be detected by sensitive techniques such as, but not limited to, light scattering, viscosity, or conductiometric approaches that are conventionally used in the testing for blood coagulation dysfunctionality. It will also be appreciated that the rate of fibrin polymer production will be dependent on concentration of free thrombin, and thus directly related to the concentration of CSSF and excess SSF added to the analyte solution at the outset of the diagnostic test.

The invention is further described by the following examples which are offered by way of illustration and are not intended to limit the invention in any manner. In these examples all percentages are by weight if for solids and by volume if for liquids, and all temperatures are in degrees Celsius unless otherwise noted.

EXAMPLE 1

Preparation of a Thrombin Binding Oligonucleotide Ligands

Oligonucleotides with the structure $5'$GGTTGGTGTGGTTGG$3'$ (SEQ ID NO: 1) known to bind and inhibit thrombin (hereafter referred to as the "consensus ligand") were prepared essentially as described in Bock, L. C. et al., *Nature,* 355, 564 (1992) using standard phosphoramidite chemistry on a Applied Biosystems DNA synthesizer. Minor modifications of the same procedure were used to make a variant molecule $5'$AT<u>GGTTGGTGTGGTTGG</u>TCGAGCTAGATCTTCAGTACGT$3'$ (SEQ ID NO: 2) hereafter referred to as the "tailed ligand". This molecule contains within it a subsequence (underlined) identical to the consensus ligand sequence. The consensus ligand subsequence is responsible for the thrombin-binding properties of the tailed ligand. The Watson-Crick complement of the "tailed ligand" was similarly prepared: $5'$ACGTACTGAAGATCTAGCTCGACCAACCACACCAACCAT$3'$, (SEQ ID NO: 3) hereafter referred to as the "complementary oligonucleotide" or "complement". Although this molecule is perfectly complementary to the "tailed ligand", it also contains the subsequence $5'$CCAACCACACCAACC$3'$, (SEQ ID NO: 4) which is perfectly complementary to the consensus ligand. The complement can thus hybridize to the consensus ligand as well as the tailed ligand. Interpreted in terms of the strategy of equations (1) and (2) of the invention, SSF corresponds to either the consensus or the tailed ligands and CSSF corresponds to the respective complementary oligonucleotide.

Using similar processes, bi-directional oligonucleotide ligands have been prepared by connecting two copies of the following sequences to a linker compound through their respective 3' ends: 5'-GGTTGGT-3' (SEQ ID NO: 5); 5'-GGTTGGTT-3' (SEQ ID NO: 6) and 5'-GGTTGGTTG-3' (SEQ ID NO: 7). Specifically, these oligonucleotides with reverse sequence polarity connected through a single phosphodiester linkage were prepared essentially as described by van de Sande, J. H. et al. *Science* 241, 551 (1988). The compounds were prepared by solid-phase synthesis on an Applied Biosystems DNA synthesizer using standard phosphoramidite coupling chemistry with some special reagents as described below.

To prepare oligonucleotides containing 3'-3' internucleotide linkages, synthesis was first performed in the 5'→3' direction beginning with 5'-derivatized CpG columns (dG-5'-Icaa CpG, 1 μmole, Glen Research) and 5'-phosphoramidites (dT-5"-CE phosphoramidite and dG-5'-CE phosphoramidite from Glen Research). Subsequent coupling cycles were repeated in the 5'→3' direction until the first of the two bi-directional segments was complete. The direction of synthesis was reversed from 5'→3' to 3'→5', by simply replacing 5'-phosphoramidites with standard 3'-phosphoramidites (ABI). The first linkage formed after the reversal of synthesis direction was a 3'-3' internucleotide linkage. Subsequent couplings were repeated in the 3'→5' direction (forming 3'-5' linkages) until the second of the two bi-directional segments was complete.

After the synthesis and following detritylation, the oligonucleotides were released from the CpG columns and deprotected by treatment with concentrated ammonia (12–14 hours, 56° C.). The oligomers were then purified by denaturing gel electrophoresis, followed by ethanol precipitation.

The following bi-directional compounds were prepared by this method:

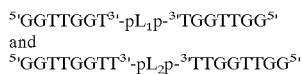

where $L_1$ represents the hexaethylene glycol chain ($-CH_2CH_2-(OCH_2CH_2)_4-OCH_2CH_2-$) linked at each end to a phosphodiester linkage p, where p=— $\underline{O}$—PO(O)—$\underline{O}$— where the underlined oxygen atoms are attached directly to either end of the hexaethylene glycol chain or the 5' or 3' position of the pentose moieties of the flanking nucleotides, and $L_2$ represents the glycerol derivative ($-CH_2-CH(OH)-CH_2-$) linked at each end to an oligonucleotide segment through phosphodiester linkage p as described above.

EXAMPLE 2

Inhibition of Thrombin Conversion of Fibrinogen to Fibrin

This example demonstrates inhibition of thrombin conversion of fibrinogen to fibrin in whole platelet-poor porcine plasma ($P^4$) by the ligands prepared in Example 1.

$P^4$ was prepared by separating cells from serum by centrifugation of whole citrated porcine blood (Environmental Diagnostics Inc). Approximately 0.5 mL of $P^4$ was added to 13×100 mm glass test tubes (Fisher) and equilibrated to room temperature in a water bath for 15 minutes. Following equilibration, varying amounts of both the consensus and tailed ligands in saline were added along with sufficient saline diluent to bring the total volume to 0.55 mL. The amounts of each ligand added are seen in FIG. 1. At this time, 50 μL of 0.4M $CaCl_2$ was added to initiate coagulation and the tubes were quickly capped. Tube contents were mixed on a laboratory inverting mixer and time of coagulation noted for each tube type by a sharp change in fluid mixing associated with the transition from liquid to gel state. FIG. 1 illustrates results of the coagulation time assay for the consensus and tailed ligands demonstrating inhibition of thrombin in plasma. Briefly, clotting or coagulation time increased with increasing concentration of both consensus and tailed ligand.

Similar inhibition of thrombin in plasma was demonstrated with the bi-directional oligonucleotide ligands prepared in Example 1 using the following methodology. Whole platelet-poor porcine plasma (PPP) was prepared by separating cells from serum by centrifugation of whole citrated porcine blood (Environmental Diagnostics Inc.). Approximately 0.5 ml of PPP was added to 12×75 mm polystyrene test tubes (FALCON, Becton Dickinson) and equilibrated to room temperature in a water bath for 15 minutes. Following equilibration, 25 μl of 250 μg/ml bovine thrombin (Sigma) in saline was added along with varying amounts of bidirectional nucleic acid ligand compounds prepared in Example 1 in saline and sufficient saline diluent to bring the total volume to 0.6 ml. At this time 50 μl of 0.4M $CaCl_2$ was added to initiate coagulation and the tubes were quickly capped. Tube contents were mixed on a laboratory inverting mixer and time of clotting noted for each tube type. Both of these bi-directional nucleic acid compounds also demonstrated inhibition of exogenous thrombin in plasma.

EXAMPLE 3

Rapid Reversal of Thrombin Inhibition

This Example demonstrates rapid reversal of the anticoagulated state induced by ligand-bound thrombin and initiation of coagulation of $P^4$ by thrombin released from the ligated state in the presence of a reversing agent.

$P^4$ was prepared as described in Example 2, and the measurement of coagulation time was also performed as Example 2. In this Example, the final total volume (0.5 mL $P^4$, 50 μL of 0.4M $CaCl_2$, optional consensus ligand of Example 1, optional tailed ligand of Example 1, optional complement (reversing agent) to the ligand sequence, and saline diluent) was held constant at 0.625 mL by adjusting saline diluent volumes.

In the control without added ligand or complement, 75 μL saline diluent was added to 0.5mL $P^4$ with 50 μl $CaCl_2$ solution. For experiments with added ligand, only 62.5 μL saline diluent was added along with 12.5 μL of a 500 μM consensus or tailed ligand solution. In reversed experiments where both ligand and complement (reversing agent) were added, only 37.5 μL saline diluent was added to tubes with the remaining 25 μL reserved for subsequent addition of 500 μM complement (reversing agent) solution.

The results of this Example are shown in FIG. 2 in which the left-most bar is the coagulation time of $P^4$ in glass tubes (control tubes). This demonstrates that thrombin is released from prothrombin present in $P^4$ by contact with the glass test-tube surface. Addition of tailed and consensus ligands to $P^4$ inhibits coagulation as illustrated in the next two bars, which is consistent with the data of Example 2, by binding to thrombin as it is produced from prothrombin by contact with the glass tube surface. Interpreted in terms of equation (1) of this invention, SSF+thrombin=SSF-thrombin, where SSF is either consensus or tailed ligand.

The fourth and fifth bars show that, when the reversing agent (complement to the tailed ligand) is added to tubes identical to those represented by the second and third bars (at the time control glass tubes coagulated), rapid coagulation occurs instead of remaining in a temporary anticoagulated state. Interpreted in terms of the strategy of equation (2) of this invention, SSF-thrombin+CSSF=thrombin+DSF, and the released thrombin rapidly converts fibrinogen to fibrin, causing $P^4$ to coagulate.

The final bar of FIG. 2 is the result of a control experiment that demonstrates that the complement is not a thrombin ligand and thus does not significantly inhibit coagulation significantly above control values.

Similar reversal of the inhibition of thrombin by the bi-directional nucleic acid compounds is expected with appropriate complementary reversing agents.

The invention disclosed herein is not limited in scope to the embodiments disclosed herein. Appropriate modifications, adaptations and expedience for applying the teachings herein in individual cases can be employed and understood by those skilled in the art within the scope of the invention as claimed herebelow.

That which is claimed is:

1. A kit for the reversible anticoagulation of blood comprising: a nucleic acid ligand which binds thrombin, said nucleic acid ligand selected from the group consisting of a nucleic acid ligand having SEQ ID NO:1, a nucleic acid ligand having SEQ ID NO:2, a bi-directional nucleic acid ligand comprising two oligonucleotide segments having SEQ ID NO:5 linked at their respective 3' ends to a phosphodiester group each of which is linked to a hexaethylene glycol chain, and a bi-directional nucleic acid ligand comprising two oligonucleotide segments having SEQ ID NO:6 linked at their respective 3' ends to a phosphodiester group each of which is linked to a glycerol derivative; and a reversing agent which has greater affinity for the nucleic acid ligand than does thrombin, said reversing agent selected from the group consisting of compositions comprising a nucleic acid sequence complementary to that of said nucleic acid ligand, single-stranded DNA binding proteins, copper (II), mercury (II), silver (I) and platinum complexes.

2. The kit of claim 1 wherein the reversing agent comprises an oligonucleotide having a sequence complementary to the sequence of the nucleic acid ligand.

3. The kit of claim 2 wherein the reversing agent comprises SEQ ID NO:3.

4. The kit of claim 2 wherein the reversing agent comprises SEQ ID NO:4.

5. The kit of claim 1 packaged in a specimen collection container.

6. The kit of claim 5 wherein said specimen collection container comprises an evacuated tube having a closed end and an open end covered by a septum.

7. The kit of claim 6 wherein said evacuated tube is a plastic tube.

8. A method of reversibly anticoagulating blood using the kit of claim 1 comprising:

(a) collecting a sample of blood;

(b) adding the nucleic acid ligand to the sample; and optionally (c) subsequently adding the reversing agent to the sample.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGTTGGTGTG GTTGG                                                     15

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ATGGTTGGTG TGGTTGGTCG AGCTAGATCT TCAGTACGT           39

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ACGTACTGAA GATCTAGCTC GACCAACCAC ACCAACCAT           39

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCAACCACAC CAACC                                                     15

( 2 ) INFORMATION FOR SEQ ID NO:5:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

G G T T G G T      7

( 2 ) INFORMATION FOR SEQ ID NO:6:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

G G T T G G T T      8

( 2 ) INFORMATION FOR SEQ ID NO:7:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

G G T T G G T T G      9